US011395464B2

(12) United States Patent
Ajamian

(10) Patent No.: US 11,395,464 B2
(45) Date of Patent: Jul. 26, 2022

(54) AUTONOMOUS DRONE BEES

(71) Applicant: Arnaud Z. Ajamian, North Salem, NY (US)

(72) Inventor: Arnaud Z. Ajamian, North Salem, NY (US)

(73) Assignee: Arnaud Z. Ajamian, North Salem, NY (US)

( * ) Notice: Subject to any disclaimer, the term of this patent is extended or adjusted under 35 U.S.C. 154(b) by 395 days.

(21) Appl. No.: 16/224,683

(22) Filed: Dec. 18, 2018

(65) Prior Publication Data

US 2019/0183077 A1    Jun. 20, 2019

Related U.S. Application Data

(60) Provisional application No. 62/599,895, filed on Dec. 18, 2017.

(51) Int. Cl.
| | | |
|---|---|---|
| *A01H 1/02* | (2006.01) | |
| *G05D 1/12* | (2006.01) | |
| *B64C 39/02* | (2006.01) | |
| *B64C 33/00* | (2006.01) | |
| *B64D 47/08* | (2006.01) | |

(52) U.S. Cl.
CPC ............. *A01H 1/027* (2021.01); *B64C 33/00* (2013.01); *B64C 39/028* (2013.01); *B64D 47/08* (2013.01); *G05D 1/12* (2013.01); *B64C 2201/12* (2013.01)

(58) Field of Classification Search
None
See application file for complete search history.

(56) References Cited

U.S. PATENT DOCUMENTS

| 2016/0353661 A1* | 12/2016 | Caldeira | ................ A01H 1/027 |
| 2018/0065749 A1* | 3/2018 | Cantrell | .................... B64D 1/18 |
| 2020/0281138 A1* | 9/2020 | Chen | ..................... B64C 39/028 |

OTHER PUBLICATIONS

Robert Wood et al., Radhika Nagpal and Gu-Yeon Wei, "Flight of the Robobees", www.ScientificAmerican.com, Mar. 2013, pp. 60-65 (Year: 2013).*
Crystal Ponti, "Rise of the Robot Bees: Tiny Drones Turned Into Artificial Pollinators," https://www.npr.org/sections/thesalt/2017/03/03/517785082/rise-of-the-robot-bees-tiny-drones-turned-into-artificial-pollinators, Mar. 3, 2017 (Year: 2017).*
Edd Gent, "Robo-Bees Could Aid Insects with Pollination Duties," https://www.scientificamerican.com/article/robo-bees-could-aid-insects-with-pollination-duties/, Feb. 11, 2017 (Year: 2017).*

(Continued)

*Primary Examiner* — Peter D Nolan
*Assistant Examiner* — Demetra R Smith-Stewart
(74) *Attorney, Agent, or Firm* — Rimon PC

(57) ABSTRACT

The present application discloses a flying device designed in the shape of a bee. The flying device comprises a body with a head and a pointed tail, two wings attached to either side of the body, and one or more sensors. The one or more sensors may be located on the outer surface of the device. The sensors may include cameras for capturing pictures or videos of the environment. The sensors may also include temperature sensors (thermometers), GPS readers, and/or wind sensors (anemometer). The body of the device comprises one or more transducers and one or more processors. The device is configured to identify a type of flower or plant and to perform pollination.

20 Claims, 8 Drawing Sheets

(56) References Cited

OTHER PUBLICATIONS

Hand-pollination—Wikipedia, the free encyclopedia (archive.org) (https://www.web.archive.org/web/20120723132849/https:/en.Wikipedia.org/wiki/Hand-pollination), Jul. 23, 2012 (Year: 2012).*
"Guillermo J. Amador and David L. Hu, Sticky Solution Provides Grip for the First Robotic Pollinator, Feb. 9, 2017, Chem 2, 162-170" (Year: 2017).*
"Mostafa Ramadan Ahmed Nabawy, Design of Insect-Scale Flapping Wing Vehicles, 2015, A thesis submitted to The University of Manchester for the degree of Doctor of Philosophy in the Faculty of Engineering and Physical Sciences, pp. 1-289". (Year: 2015).*

* cited by examiner

AUTONOMOUS DRONE BEES

PRIORITY CLAIMS

The present application claims priority to U.S. Provisional Application No. 62/599,895 filed on Dec. 18, 2017 titled AUTONOMOUS DRONE BEES, the content of which is incorporated by reference in its entirety.

FIELD OF INVENTION

The present disclosure relates generally to a flying drone, and more specifically, to an autonomous flying drone designed in the shape of a bee and configured to perform pollination.

BACKGROUND

Pollination through bees has been nature's way of transferring pollen from anthers to stigmas. Disruptions due to rain, storm, or wind are inevitable. Overlooked fields or missed plants/branches also affect crop yields. Improved reliability, precision, and accuracy in pollination are desirable to increase agricultural production and bring economic benefits to farmers.

In the past decade or so, scientists have noticed that the bee population in North America is on the decline. Throughout North America and to a lesser degree around the world, bee colonies mysteriously collapse and disappear, causing huge losses in agricultural production. Many crops, from fruits to vegetables to grains, are pollinated by bees. They are greatly affected when bee colonies decline or collapse. Certain plants are more vulnerable than others because they depend on a single species of bees for pollination and may face the danger of extinction if that single bee species dies out.

The present disclosure teaches advantageous man-made devices designed to solve the aforementioned problems.

SUMMARY

Accordingly, it is an objective of this disclosure to set forth devices and apparatus designed to fly over designated plants and perform pollination like real bees. The devices and apparatus are equipped with pattern recognition capability to identify a certain type of plant or crop, and are configured to collect pollen from anthers and release the collected pollen onto stigmas, performing pollination within a predetermined area.

In one embodiment, a device made in a bee shape comprises a body, a pointed tail, two wings attached to either side of the body, and one or more sensors. In some embodiments, the one or more sensors are located on the outer surface of the device. The sensors may include cameras for capturing pictures or videos of the environment. The sensors may also include temperature sensors (thermometers), GPS readers, and/or wind sensors (anemometer). The body of the device may comprise one or more transducers and one or more processors. The transducers are configured to actuate the movements of the wings. The one or more processors are configured to process the data collected by the sensors and control the movements of the device via the transducers.

In some embodiments, the processors are configured to navigate a flight path of the device through pattern recognition. For example, the processors are configured to autonomously determine the flight path by identifying a pollination target as a first destination. The pollination target may be a flower. By controlling the movements of the device using the transducers, the processors can direct the device to approach and make contact with the flower. In some embodiments, the body of the device may be covered by a swatch of fabric or Velcro. When in contact with an anther, the fabric or Velcro swatch picks up pollen bits or sacs. The pollen or a portion of the collected pollen is released when the device flies to a stigma of the same flower or the same type of flowers as determined by the processors. In some embodiments, the device may be configured to stop at multiple anthers, to ensure enough pollen has been collected, before flying to a stigma. Through repeated pollen collection and release, the device performs pollination like a real bee.

In some embodiments, the device comprises one or more transceivers for transmitting and receiving data. The one or more transceivers may include Bluetooth, WiFi, cellular, or satellite data transmitters and receivers. Through the transceivers, the device can communicate with a GPS server, for example, to receive location information of the device itself or the pollination target. The device can communicate with a server to receive different types of information, for example, the crop location, the pollination target, or other instructions related to performance of the pollination task.

In some embodiments, the device receives the crop's geographic data, for example, the crop field's longitudes and latitudes, from a server before navigation. The processors determine a designated pollination area based on the geographic data of the crop. During the flight, the processors can use the designated pollination area to ensure that the device's flight path is within the designated area.

In some embodiments, the device substantially resembles a real bee in shape and size. The device has an elongated body with a pointed tail. The body of the device is made of a light material, such as polycarbonate. The size of the device is substantially the same as a real bee. In one embodiment, the length of the body is approximately 2.5 cm, the width of the body is approximately 2.0 cm, and the height of the body is 1.5 cm. The device further includes a pair of wings that are attached to either side of the body. The wings are made of materials that are light and durable. The wing material is selected based on the requisite density, strength and durability. In one embodiment, the length of the wing is 2.0 cm and the total wing span of the device is 6 cm.

To reduce power consumption and to lengthen the flight time before the battery runs out, it is desirable that the body be light. An important criterion for selecting the body material and the wing material is density. Also the internal components of the device, e.g., the processors, transducers, and sensors, are designed to be small and light in order to fit into the body of the device and to avoid adding too much weight to the entire device. In one embodiment, the device weights approximately 120 mg.

In some embodiments, the device is powered by a battery. In one embodiment, the battery is rechargeable. In one embodiment, the processors are configured to direct the device to return to a charging station before the battery runs out. In one embodiment, the device is powered by solar energy. The battery of the device stores the energy converted from solar energy by a solar panel. In one embodiment, the device is powered by solar energy during the day and by battery at night. In another embodiment, the device comprises a piezoelectric device configured to harness vibration energy of the wings and convert the vibration energy into electric energy.

In some embodiments, the device is equipped with sensors such as cameras, distance sensors, temperature sensors, wind sensors, and/or GPS readers. One or more cameras may be a normal camera configured to capture flight images or videos during the day while the device is flying in the air. One or more cameras may be a night vision camera to enable the device to operate at night. Temperature sensors and wind sensors can be used to provide additional data in aid of navigation. For example, the reading of the wind direction from the wind sensors can be used to steer the device in a direction that is more energy efficient.

In some embodiments, the distance sensors provide readings to the processors for determination of the distance between the device and the pollination target. Based on the distance, the processors can control the movements of the wings to allow the device to approach a pollination target and to align itself with the pollination target.

In some embodiments, the processors onboard the device are configured to autonomously determine the flight path of the device based on data collected from the various sensors. In some embodiments, the device receives flight instructions from a remote server. In other embodiments, the device is configured to determine a flight path based on information received from a remote server and data collected from a remote server or the various sensors on board.

In the descriptions set forth below, the advantageous devices and apparatus disclosed herein are also referred to as drone bees or autonomous drone bees. The use of such terms reflects certain characteristics of the devices and apparatus described herein but otherwise does not incorporate common or known features of prior art that are not explicitly mentioned.

BRIEF DESCRIPTION OF THE DRAWINGS

These and other features of the present disclosure will become readily apparent upon further review of the following specification and drawings. In the drawings, like reference numerals designate corresponding parts throughout the views. Moreover, components in the drawings are not necessarily drawn to scale, the emphasis instead being placed upon clearly illustrating the principles of the present disclosure.

DETAILED DESCRIPTION

Embodiments of the disclosure are described more fully hereinafter with reference to the accompanying drawings, in which preferred embodiments of the disclosure are shown. The various embodiments of the disclosure may, however, be embodied in many different forms and should not be construed as limited to the embodiments set forth herein. Rather, these embodiments are provided so that this disclosure will be thorough and complete, and will fully convey the scope of the disclosure to those skilled in the art.

The present disclosure teaches a drone bee designed to perform pollination efficiently. There was prior effort to create robotic bees that could perform pollination by suction. However, in the prior effort, both design and engineering problems render it difficult to commercially deploy drone bees in the field to aid pollination of crops and plants. For example, in prior art, drone bees are not equipped with cameras for pattern recognition, thus cannot be configured to collect pollen from a specific type of flower or release pollen to the same type of flower.

For another example, one prior art reference describes a robotic bee that "sucks in pollen from a plant and expels it onto others." For suction of pollen to take place, the robotic bee would need to carry a miniaturized vacuum. Carrying a miniaturized vacuum during flight presents many engineering problems. For instance, because of the weight of the vacuum, it would be difficult to control the overall weight of the robotic bee and to maintain stability during flight. More importantly, the movements of the wings or propellers can interfere with suction. The vacuum must provide stronger suction to overcome the thrust from the wings or propellers.

Furthermore, in all known commercially available drones, a pilot is required to remotely control the drone to take off, and to fly and land safely, and more importantly, to make sure the flight is in compliance with Federal Aviation Agency rules. The devices disclosed herein can be configured to fly autonomously by relying on pattern recognition software. Also the drone bees disclosed herein are designed for the specific purpose of pollination. They pose little safety issues commonly associated with other types of commercial drones. For example, the drone bees disclosed herein are configured to fly at a very low altitude so that they do not interfere with commercial airplanes. For another example, the drone bees disclosed herein can be configured to fly autonomously by setting pollination targets as destinations, thus eliminating the need of pilots, avoiding pilot errors, and preventing federal violations. The following disclosure sets forth the detailed description of how to make and use the pollination drone bees.

Figure 1:
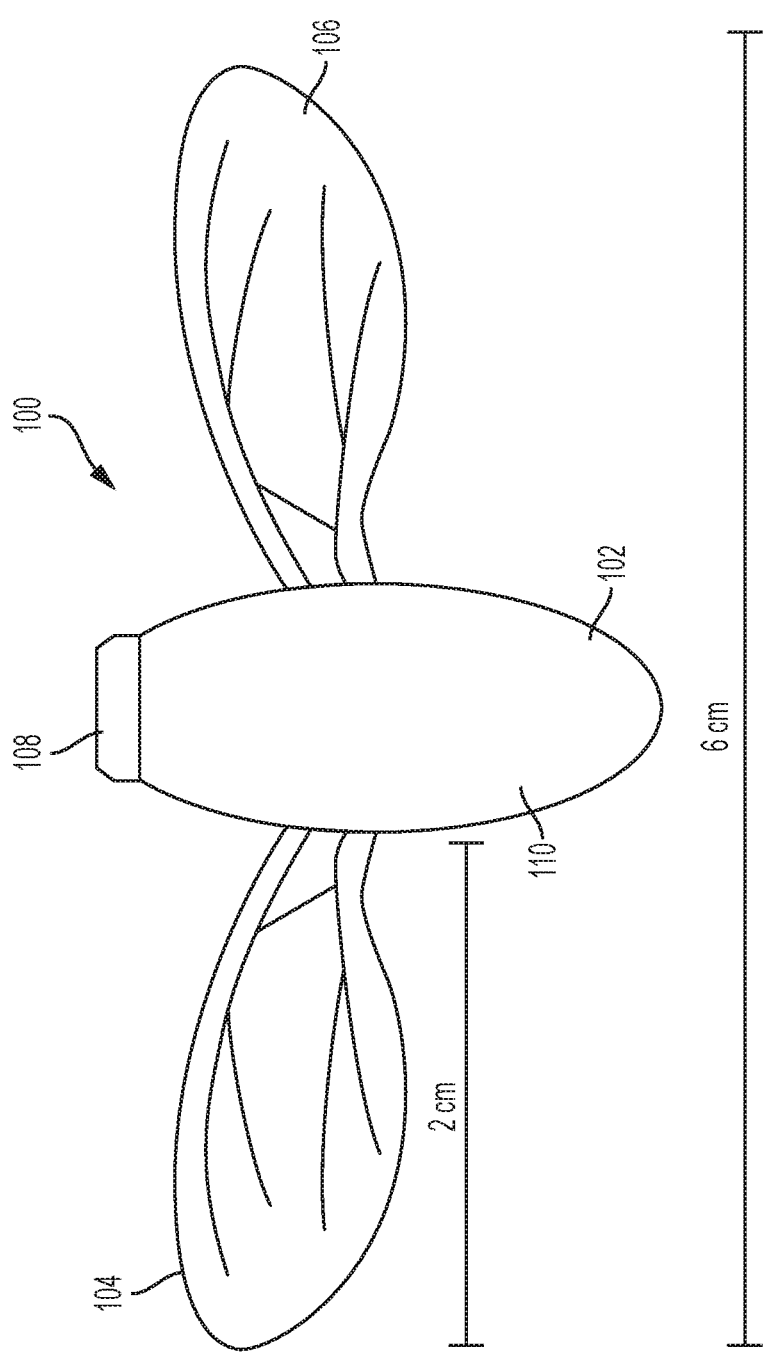
FIG. 1 illustrates an exemplary drone bee.

In referring to FIG. 1, an exemplary flying device 100 in the shape of a bee is depicted. The flying device, herein also referred to as drone bee, comprises a body 102 and two wings 104, 106. The body 102 comprises a head 108 and a pointed tail 110. To facilitate flying, the body 102 is hollow and the body casing is made of light material. In one embodiment, the body casing is made of polycarbonate. The two wings 104, 106 are attached to either side of the body 102. The drone bee is substantially similar to a real bee in shape and size.

Figure 2A:
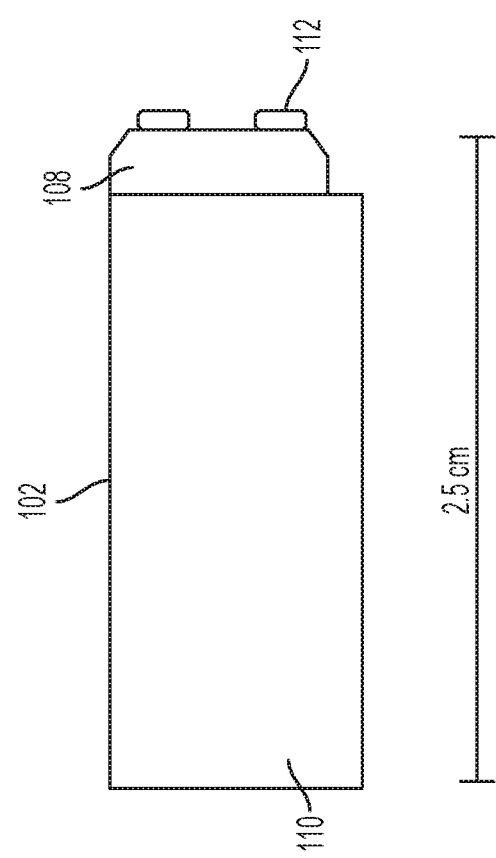
FIG. 2a illustrates a side view of an exemplary drone bee.

The exemplary drone bee 100 shown in FIG. 1 has a body 102 of dimensions 2.5 cm×2.0 cm×1.5 cm, as illustrated in FIG. 2a. The size of the body 102 is substantially the same as one of the two wings 104, 106. Each wing is approximately 2 cm long and the total wing span is 6 cm. It is noted that the sizes shown in FIG. 1 and FIG. 2a are for illustration purposes and should not be interpreted as limiting. The exemplary drone bees can be made into other suitable body sizes, body components and proportions.

The body 102 is hollow and can accommodate various electrical and mechanical components, such as processors, transducers, signal receivers and transmitters, etc. The body 102 comprises the head 108 and the tail 110. The head 108 may comprise one or more cameras 112. The cameras 112 may be binocular or monocular. In FIG. 2a, two cameras 112 are shown to be located on the head 108. In one embodiment, the cameras 112 may be located on the front or top of the head 108. In another embodiment, the cameras 112 may be located on the underside of the head 108, facing downward to allow the cameras 112 to capture images of the field beneath the drone bee.

In one embodiment, at least one of the cameras 112 may be a normal camera suitable for use during the day. In another embodiment, at least one of the cameras 112 may be a night vision camera suitable for use at night. When the drone bee 100 is equipped with a normal and a night vision camera, the drone bee can work day and night, allowing it to work more hours in a day if needed to meet a deadline or to avoid bad weather, for example. In one embodiment, the drone bee 100 may be equipped with other types of cameras or video recorders. The images or videos taken by the cameras may be stored in memory devices carried by the drone bee 100 or sent to the processors for imaging processing. Pattern recognition software may be used to analyze the images taken by the cameras in order to identify a specific type of flower designated as pollination target.

Figure 2B:
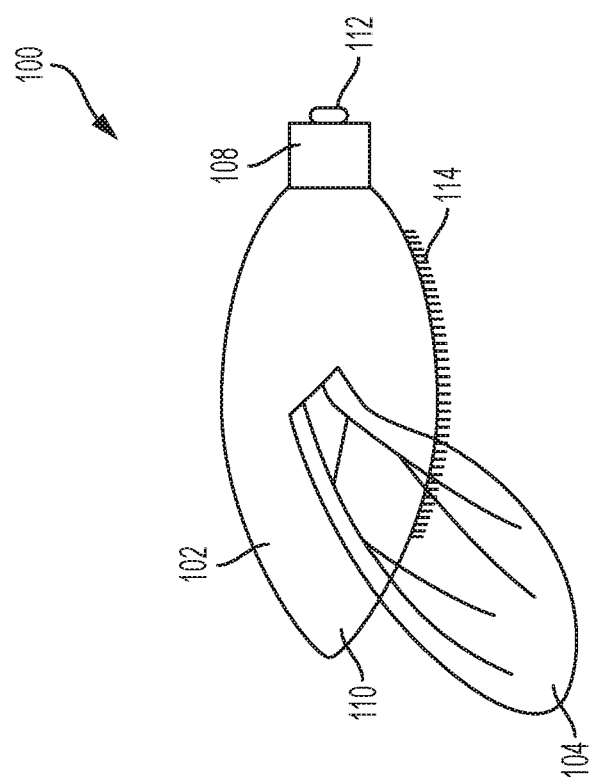
FIG. 2b illustrates another side view of an exemplary drone bee.

FIG. 2b illustrates a second side view of the body 102 of the exemplary drone bee 100. The body 102 is elongated and resembles the body of a real bee. However, in some embodiments, the body 102 may be shaped differently. For example, the contour of the body 102 may be shaped angularly at one or more locations. In one embodiment, the upper side of the body 102 may be smooth but the underside of the body 102 may be angular, for example, rectangularly shaped. In FIG. 2b, the underside of the body 102 is covered by a piece of coarse fabric or a swatch of Velcro 114. The cover 114 is used to collect pollen when in contact with the anther of a flower. Compared to the suction mechanism used in prior art to pick up pollen, the use of fabric or Velcro is cheaper, simpler, and more effective and energy efficient. Unlike the suction mechanism, the cover 114 weighs little and collects pollen by simply touching the anther. Therefore, there is no danger of pollen being blown away by the moving wings or propellers. Moreover, using the cover 114 to collect pollen does not consume power, thus conserving energy and enhancing battery life. When it is time to release collected pollen onto a stigma, the drone bee 100 approaches the stigma. Bits or sacs of the pollen affixed to the fabric or Velcro are knocked off when the cover 114 comes into contact with the stigma. It is noted that the process of collecting and releasing pollen by the cover 114 emulates the pollinating process of a bee. When a bee stops on an anther, the tiny hairs on the bee's legs pick up pollen from the anther. Tiny pollen particles cling to the bee hairs, the same way they cling to a piece of coarse fabric or Velcro. The pollen particles do not fall off during flight. When the bee lands on the next flower, a few pollen particles will be dislodged and fall onto a stigma.

A drone bee 100 may be equipped with a variety of sensors to aid navigation and flight. For example, cameras 112 may be installed to capture images or videos for pattern recognition and image processing. Wind sensors can be installed on the surface of the body 102 to measure the strength and direction of the wind. Readings from a wind sensor can be used for flight control, e.g., selecting a more energy efficient route, or for navigation, e.g., selecting a flight direction that takes into account of the blow of the wind. Other sensors can be installed on the surface of the body 102 to measure temperature, humidity, and/or pressure. In some embodiments, the drone bee 100 may be equipped with a distance sensor to measure the distance to a pollination target. The reading from a distance sensor can inform the drone bee 100 that it is approaching a pollination target. In such case, the drone bee 100 may be configured to slow down or turn around to align itself with the target. In some embodiments, the drone bee 100 may carry a GPS reader, the readings of which provide location information of the drone bee 100. The drone bee 100 may transmit its location information to a remote server for tracking purposes. Alternatively, the drone bee 100 can carry a tracking device to allow a remote server to track its location as it flies around.

Figure 3A:
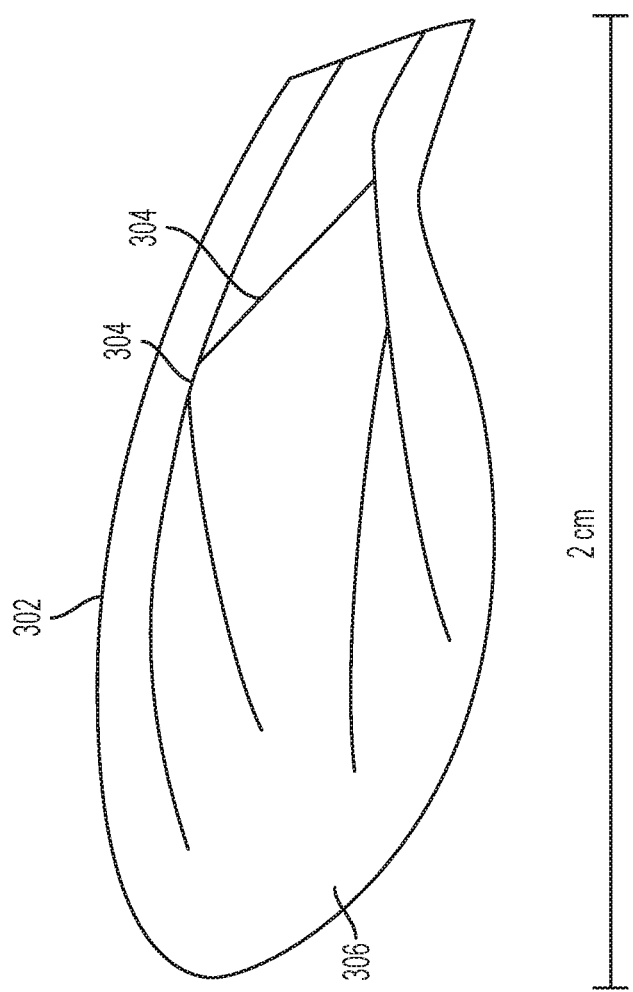
FIG. 3a illustrates an exemplary wing of an exemplary drone bee.

The drone bee 100 is constructed with two wings 104, 106 that are made of light and durable materials. Preferred materials include carbon fiber that meets the requirements of requisite density and strength. In some embodiments, the wings 104, 106 comprise a frame 302 with one or more ribs 304 as support. The wings 104, 106 are covered by a piece of skin 306. The dimensions of the wings 104, 106 are substantially similar to those of a real bee. In one embodiment, the length of the wing 104, 106 is approximately 2 cm, as shown in FIG. 3a. The shape of the wing 104, 106 may resemble that of a real bee as shown in FIG. 3a. In some embodiments, the shape of the wing 104, 106 may be different from that of a real bee, to accommodate various design considerations, such as manufacturing costs, material limitations, etc.

Figure 3B:
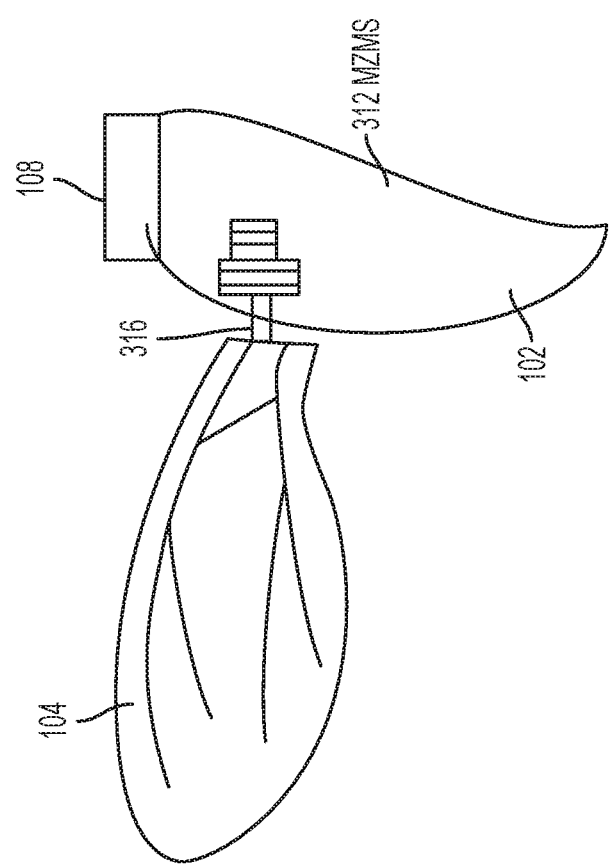
FIG. 3b illustrates an exemplary joint that connects a wing to the body of an exemplary drone bee.

The wings 104, 106 are attached to either side of the body 102 and are connected to the same or different transducers. As shown in the exemplary embodiment of FIG. 3b, the two wings 104, 106 are attached to two transducers 312 respectively. Only one transducer 312 is shown in FIG. 3b. The two transducers 312 are actuators configured to actuate the movements of the wings. They are separately controlled by computer processors (see FIG. 6) so that the two wings 104, 106 are independently controlled. The two wings 104, 106 can move or flap at different rates and in different orientations to provide mobility and agility. In some embodiments, the drone bee 100 can fly up and down, hover above a target and land on a target with little or no thrush. The drone bee 100 can also turn around by flapping one wing stronger or faster than the other.

In some embodiments, the transducers 312 may be made of microelectromechanical systems (MEMS). As shown in FIG. 3b, MEMS transducers 312 convert power into mechanical movements. Through coupling mechanism 316, the mechanical movements are converted into flapping movements of the wing 104.

In some embodiments, the drone bee 100 carries a battery as the power source. MEMS devices may be used to convert the electric energy of the battery into mechanical movements. Because the size of the drone bee 100 is small and the energy it consumes is also small, energy harvesting can be effectively used as supplemental power source in addition to the battery carried onboard by the drone bee 100. In some embodiments, solar panels are installed on the surface of the drone bee 100. The solar energy harvested by the solar panels is converted into electric energy/chemical energy stored in the battery. In some embodiments, piezoelectric materials may be installed to convert vibrational energy of the drone bee 100 into electric energy. Well known piezoelectric materials include quartz, synthetic crystals, synthetic ceramics, polymers, and nanostructures. Piezoelectric materials generate electric potential when experiencing mechanical stress. For example, the electric dipoles inside a typical piezoelectric material become aligned when pressure is applied on the material, inducing a voltage between two spots on the surface of the material. When connected to a battery, the induced voltage can re-charge the battery, converting mechanic energy into electricity.

Powered by the battery carried onboard, the drone bee 100 is autonomous. It can be self-directed and self-driven. The cameras act as the "eyes" of the drone bee 100 and the various sensors act as the "antennas." In one exemplary embodiment, the drone bee 100 is designed and configured for pollination.

Figure 4:
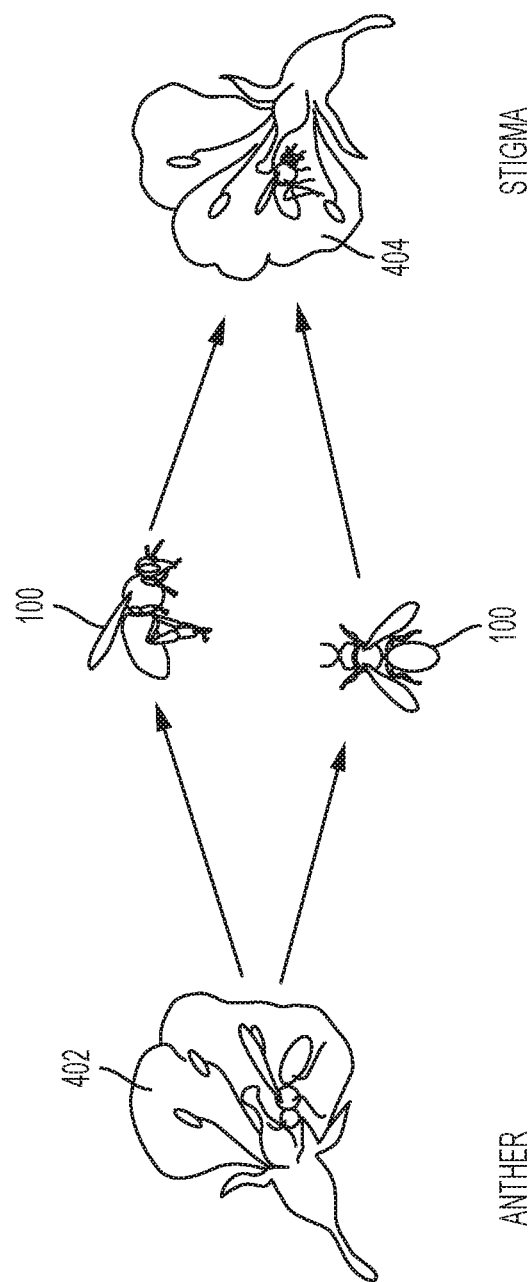
FIG. 4 illustrates an exemplary flight path of the exemplary drone bee between two pollination destinations.

In such an embodiment, before taking off, the drone bee 100 uploads the geographic location of a crop field, e.g., the longitudes and latitudes of the four corners of the crop field. Through guidance of a GPS system, the drone bee 100 flies to the crop field to assist pollination. Through pattern recognition, the drone bee 100 identifies the pollination target, e.g., a flower. As the drone bee 100 approaches the pollination target, the cameras 112 zooms in to the inside of the flower and identifies the anther 402 of the flower as its first destination. The anther 402 is where the pollen of the flower is stored. See FIG. 4. The distance sensor or sensors measure the distance between the drone bee 100 and the anther. As the distance between the drone bee 100 and the anther approaches zero, the drone bee 100 prepares for landing by slowing down and aligning itself with the anther so that the cover 114 can make contact with the anther. The cover 114 acts like the hair of the drone bee 100 and picks up the pollen bits or pollen sacs from the anther. The cover 114 may be a piece of coarse fabric or Velcro that provides sufficient friction to prevent pollen from falling off when the drone bee 100 takes off again.

After the first destination, the drone bee 100 may be configured to choose a stigma 404 of the same flower or the same type of flower as its second destination. In an alternative configuration, the drone bee 100 may stop on two or more anthers to collect sufficient pollen before approaching a stigma to release the collected pollen. When the distance sensor or sensors indicate that the drone bee is near its second destination, the drone bee 100 prepares for landing by slowing down and aligning itself with the stigma. Once the drone bee is in contact with the stigma, a few pollen bits or sacs are dislodged and released from the cover 114. The dislodged pollen bits fall into the stigma to fertilize the ovary that will grow into fruits.

Figure 5:
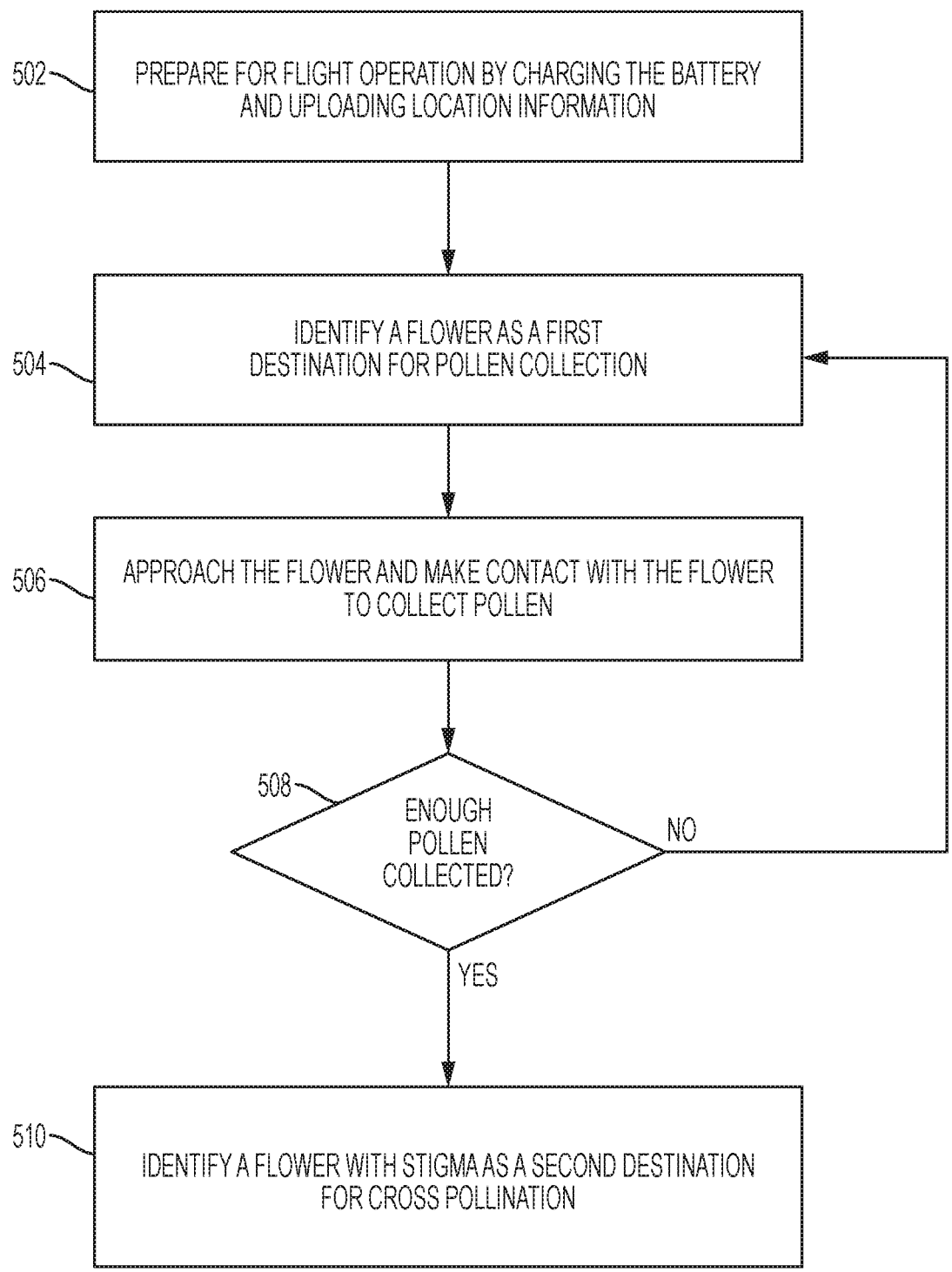
FIG. 5 is a flow chart illustrating an exemplary pollination process of the exemplary drone bee.

FIG. 5 is an exemplary flow chart illustrating a pollination process performed by the drone bee 100. In step 502, the drone bee 100 prepares for an upcoming flight operation by fully charging the battery and uploading the location information of the crop field. The location of the crop field may be the geographic data of the crop field, e.g., the longitudes and latitudes of the corners, or the center location and the diameter of a circular field. The location of the crop field may be a set of flight directions. After the preparation, the drone bee 100 takes off. The cameras 112 capture images while the drone bee 100 is in the air. In some embodiments, the cameras 112 are configured to take pictures while the drone bee 100 is en route to the crop field. In some embodiments, the cameras 112 are configured to start taking pictures when the drone bee 100 has reached the crop field. The images are processed by pattern recognition software installed onboard, and are used to direct the flight operation of the drone bee 100.

In step 504, the drone bee 100 identifies a flower in the images as the target flower for pollination. It sets the flower as a first destination for pollen collection. The drone bee 100 approaches the flower and makes contact with the anther of the flower (step 506). The cover 114 of the drone bee 100 picks up pollen bits or pollen sacs when it touches the tip or head of the anther. In some embodiments, the drone bee 100 sets off to release pollen after making a stop at the anther. In other embodiments, the drone bee 100 may be configured to stop at more than one anther to ensure that enough pollen has been collected (see step 508). The number of anther stops may be pre-determined based on weather condition and/or flower characteristics. The number of anther stops may be determined dynamically and/or autonomously by the drone bee 100, based on data collected by the temperature sensors and wind sensors or results from image processing.

In step 510, the drone bee 100 searches a stigma 404 to release pollen. The stigma 404 is first identified among the images and then set as a second destination. The drone bee 100 approaches the stigma and makes a stop. A few of the pollen bits or sacs attached to the cover 114 are dislodged and fall off the cover 114 onto the stigma 404. Afterwards, the drone bee 100 may be set off to another stigma or anther, depending on its pre-configuration or real-time decision.

In some embodiments, the drone bee 100 is autonomous and is powered by battery carried onboard. The battery is pre-charged before the flight. In one embodiment, the drone bee 100 carries solar panel to collect solar energy. The solar energy may be used to recharge the battery and reduce the number of return trips for battery recharging. In one embodiment, the drone bee 100 may be completely powered by solar energy. In some embodiments, MEMS sensors can be used to harvest environmental energies (wind energy, vibrational energy, or electromagnetic field energy) to power the drone bee 100.

Figure 6:
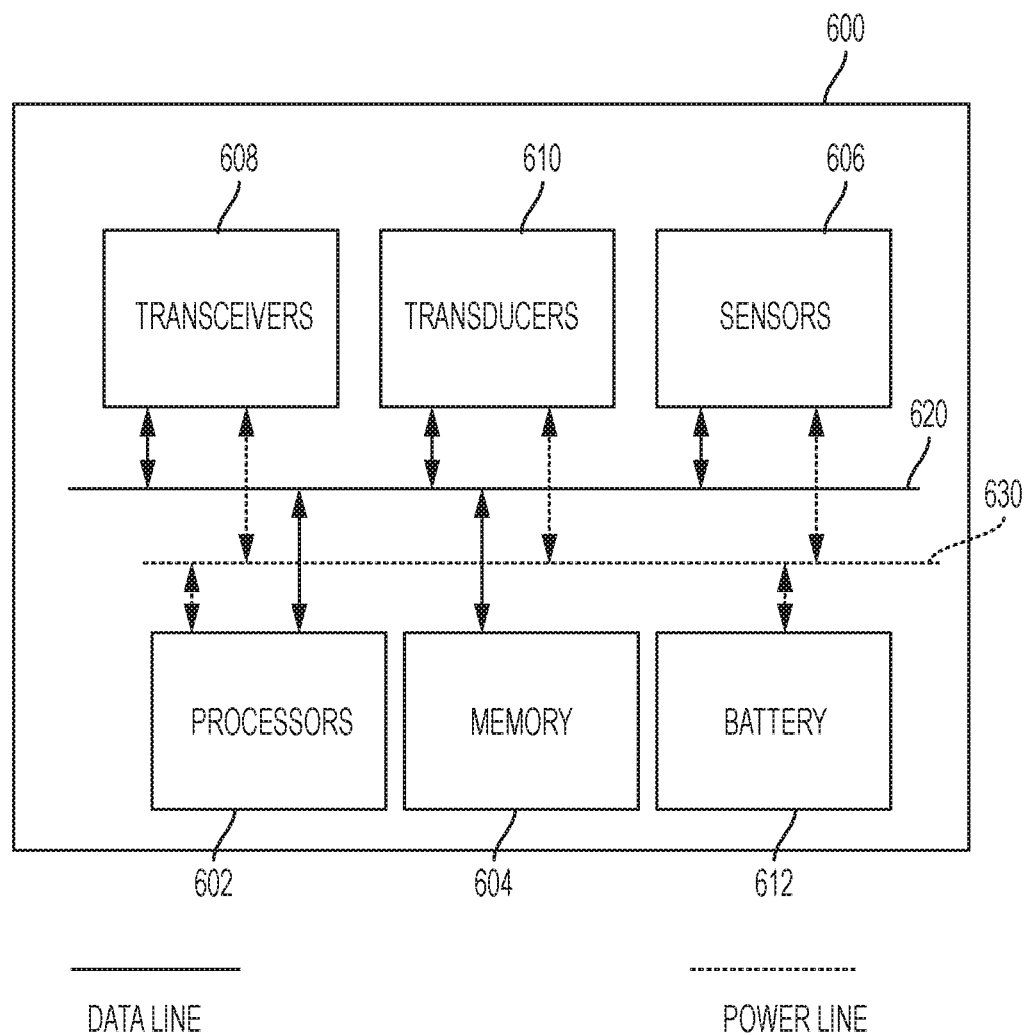
FIG. 6 is a block diagram illustrating exemplary components of the drone bee.

FIG. 6 is a block diagram illustrating exemplary components of a drone bee 100. As shown in FIG. 6, the drone bee 100 comprises processors 602 and memories 604 for the various computation tasks described herein. The processors 602 and memories 604 are configured to process and store data generated by the various sensors 606. Examples of the sensors 606 installed on the drone bee 100 include cameras, wind sensors, temperature/pressure/humidity sensors, GPS readers, etc. The readings from the sensors 606 are stored in the memory 604 and processed by the processors 602. In some embodiments, the drone bee 100 communicates with a remote server via cellular or WiFi or Bluetooth network and may be configured to transmit the sensor data to the remote server for further processing. For that purpose, the drone bee 100 may be equipped with wireless transmitters and receivers 608. The transceivers 608 are configured to transmit and receive wireless data through an antenna installed on the drone bee 100. In some embodiments, the drone bee 100 is configured to autonomously control its flight operation with little or no interaction with a remote server. In some embodiments, the drone bee 100 may be configured with limited computing power and may rely on a remote server for directions and commands. The processors 602 either interprets the commands the drone bee 100 receives from a remote server or generates commands in-situ after processing and computing the sensor data. Using the commands, the processors 602 control the movements of the drone bee 100 via transducers 610.

In some embodiments, the drone bees are equipped with two wings connected to two transducers 610 respectively. The processors 602 control the transducers 610 separately and the wings can move independently of each other. In other embodiments, the wings may be configured to move synchronously. In yet another embodiment, the drone bee 100 may be equipped with a propeller (not shown) configured to provide lift power. The propeller may be configured to work without or in aid of the wings 104, 106.

As shown in FIG. 6, the processors 602 are connected to all other components via a data line 620 for data communication. All components are connected to the battery 612 via a power line 630. In some embodiments, the battery 612 provides power to the electronic components but does not power the movements of the drone bee 100. The drone bee 100 may be connected to a power source via an electric wire.

In some embodiments, the battery 612 provides power to the mechanical parts of the drone bee, allowing the drone bee 100 to move freely without being tied to a ground power source. In some embodiments, the drone bee 100 may be powered or charged via wireless power transmission.

Although the disclosure is illustrated and described herein with reference to specific embodiments, the disclosure is not intended to be limited to the details shown. Rather, various modifications may be made in the details within the scope and range of equivalents of the claims and without departing from the disclosure.

What is claimed is:

1. A device in the shape of a bee, comprising:
    a body with a head and a pointed tail, wherein the body comprises one or more transducers and one or more processors;
    two wings attached to either side of the body; and
    one or more sensors;
    wherein the one or more sensors include two cameras located on the front of the head, said cameras being used to capture digital images that are fed to the one or more processors for pattern recognition processing;
    wherein the underside of the body is covered by a swatch of fastening tape for pollen collection, said fastening tape made of two opposing pieces of fabric, one piece with a dense arrangement of tiny nylon hooks and the other piece with a dense nylon pile; wherein the one or more transducers are configured to actuate the movement of the wings; and wherein the one or more processors are configured to navigate a flight path of the device through pattern recognition.

2. The device of claim 1, wherein the one or more sensors include cameras, distance sensors, temperature sensors, wind sensors, or GPS readers.

3. The device of claim 1, wherein the one or more processors are configured to autonomously determine the flight path by identifying a flower as a first destination, wherein the one or more processors are configured to control the movements of the wings to approach the first destination as a pollination target.

4. The device of claim 1, further comprising one or more wireless transceivers for transmitting data to and receiving data from one or more servers.

5. The device of claim 4, wherein the device receives a crop field's longitudes and latitudes from a server before operation to determine a pollination area and wherein the one or more processors are configured to ensure that the flight path is within the pollination area.

6. The device of claim 4, wherein, when the device is approaching the flower, the one or more processors are configured to control the movement of the wings to align the device with the flower and to contact an anther or a stigma of the flower to collect or release pollen.

7. The device of claim 1, wherein the body casing is made of polycarbonate.

8. The device of claim 7, wherein the wings are made of carbon fiber having a requisite density and strength.

9. The device of claim 1, wherein the size of the device is substantially the same as a real bee.

10. The device of claim 9, wherein the length of the body is approximately 2.5 cm, the width of the body is approximately 2.0 cm, and the height of the body is approximately 1.5 cm.

11. The device of claim 9, wherein the length of the wing is approximately 2.0 cm and the total wing span of the device is approximately 6 cm.

12. The device of claim 9, wherein the weight of the device is approximately 120 mg.

13. The device of claim 1, wherein one of the two cameras is a normal camera for capturing images during the day.

14. The device of claim 1, wherein one of the two cameras is a night vision camera for capturing images at night.

15. The device of claim 1, wherein the device comprises a normal camera and a night vision camera to enable the device to operate during the day and at night.

16. The device of claim 1, further comprising a piezoelectric device that are connected to the wings and are configured to harness vibration energy of the wings and to convert the vibration energy into electric energy.

17. The device of claim 1, wherein one of the one or more sensors is a distance sensor for determining the distance between the device and a pollination target, and wherein the one or more processors is configured to control the movements of the wings according to the determined distance.

18. The device of claim 17, wherein the one or more processors is configured to control the device to make contact with the pollination target when the determined distance is approaching zero.

19. The device of claim 1, wherein the one or more transducers are powered by solar energy.

20. A device in the shape of a bee, comprising:
    a body with a head and a pointed tail, wherein the body comprises one or more transducers and one or more processors;
    two wings attached to either side of the body;
    one or more sensors; and
    two cameras located on the front of the head, said cameras being used to capture digital images that are fed to the one or more processors for pattern recognition processing;
    wherein the underside of the body is covered by a swatch of fastening tape for pollen collection; wherein the one or more transducers are configured to actuate the movement of the wings; and wherein the one or more processors are configured to navigate a flight path of the device through pattern recognition.

* * * * *